United States Patent [19]

Yanagisawa et al.

[11] Patent Number: 4,820,051

[45] Date of Patent: Apr. 11, 1989

[54] APPARATUS FOR DETERMINING MICROHARDNESS

[75] Inventors: Masahiro Yanagisawa; Yoshihiro Motomura, both of Tokyo, Japan

[73] Assignee: NEC Corporation, Japan

[21] Appl. No.: 899,334

[22] Filed: Aug. 21, 1986

[51] Int. Cl.$^4$ .................. G01B 11/22; G01N 3/00; G01N 3/48

[52] U.S. Cl. ...................... 356/378; 73/81; 73/85

[58] Field of Search ............ 356/375, 378; 250/227; 73/81-85

[56] References Cited

U.S. PATENT DOCUMENTS

| | | | |
|---|---|---|---|
| 4,147,052 | 4/1979 | Tsujiuchi et al. | 356/378 X |
| 4,275,966 | 6/1981 | Kleesattel | 356/378 |
| 4,277,174 | 7/1981 | Kleesattel | 356/378 X |
| 4,691,559 | 9/1987 | Fischer | 73/81 |
| 4,699,000 | 10/1987 | Lashmore et al. | 73/81 |

*Primary Examiner*—David Mis
*Attorney, Agent, or Firm*—Laff, Whitesel, Conte & Saret

[57] ABSTRACT

The microhardness of a specimen is determined by measuring (1) the penetration depth of an indenter which is forced into the specimen, and (2) the load applied to the indenter. The load which is applied to the indenter is preferably measured by an electrobalance. In order to detect the penetration depth of the indenter into the specimen, an optical detector is integrally connected to cooperate with the indenter. A light beam is directed toward a predetermined position where a mirror reflects the light beam in a manner which varies in response to the penetration depth of the indenter.

12 Claims, 5 Drawing Sheets

APPARATUS FOR DETERMINING MICROHARDNESS

BACKGROUND OF THE INVENTION

1. Field of the Invention

The present invention relates to an apparatus for determining the microhardness of thin films or of the surface thin layers of materials.

2. Description of Related Arts

Recently, preparation of thin films has become more and more important in various fields of electronics. In accordance with the development in thin film technology, exact evaluation of the characteristics of thin films has become and important item. Among such characteristics, their hardness or rather their microhardness is very difficult to determine.

For example, VLSI (Very large scaled integrated circuit) is manufactured by forming thin layers of a thickness around 100 nm on a substrate. If the microhardness of the thin layer of VLSI is measured directly, the quality control of the production can be conducted more effectively. Further, measurement of the microhardness of the thin layer of the magnetic disc is earnestly required to improve the abrasive resistance therof with the reading head. For the purpose of determining the microhardness of thin films, several apparatuses have been developed.

One of such apparatuses is described in Bull. Jap. Soc. Prec. Eng., Vol. 3, No. 1, (1968), p. 13. The apparatus illustrated in this article comprises a balance of counterpoised bar type. The poising bar of the balance includes at one end thereof an indenter. The other end of the poising bar is moved upwardly by means of an electromagnet to press the indenter onto a specimen, resulting in an impression on the surface of the specimen. From the value of the applied load by the electromagnet and the area of the impression measured by microscopic observation, the microhardness of the thin film is determined. In this case, observation with eyes is inevitable in determining the microhardness. In addition, the applied load cannot be determined within 0.1 grams precision because of the use of an electromagnet. Therefore, it is difficult to determine the microhardness of a thin film of the order of 0.1 microns with this apparatus.

Another apparatus is shown in Kotai-butsuri (in Japanese), Vol. 8, No. 5, (1973), p. 29-33. With the apparatus illustrated in this article, the microhardness of a specimen is determined by measuring the penetration depth of an indenter into the specimen and the load applied to the indenter for penetrating it into the specimen. With this apparatus, the indenter is driven by means of a stain gauge to penetrate into the surface of the specimen. Thus, the applied load is adjusted by varying the current applied to the strain gauge while observing the current meter of the strain gauge. On the other hand, the penetration depth is measured by means of a capacitor-type displacement measuring device connected to the indenter.

With such a measuring device, it is difficult to detect the contact between the indenter and the specimen without causing an impression to the surface of the specimen. Therefore, the applied load cannot be controlled with high precision and the initial equilibrium state cannot be set up minutely. Furthermore, the penetration depth cannot be determined within 0.01 microns precision, which is not sufficient for the determination of the microhardness of thin films of the order of 0.1 microns. Another disadvantage of the apparatus is that a plurality of measurements must be done by changing the applied load for determining correctly the microhardness of a specimen.

A similar apparatus is described in J. Phys. E: Sci. Instrum. Vol.15, (1982), P. 119-122. In this apparatus, the microhardness of a specimen is also determined by measuring the penetration depth of an indenter into the specimen and the load applied to the indenter for penetrating it into the specimen. The apparatus illustrated in this article comprises an indenter, a capacitor-type displacement measuring device fixed to the indenter, and means for applying a load to the indenter. In this case, however, the indenter is pressed to the specimen by an electrostatic force generated by the load-applying means. The applied load cannot be determined within 1 milligram precision with such load-applying means. In addition, contact between the indenter and the specimen cannot be detected clearly because of the use of a capacitor-type displacement measuring device. Another problem of the apparatus is that electronic charges in the capacitor-type displacement measuring device adversely affect the measurement of the applied load. Furthermore, surrounding conditions should be controlled because the capacitor-type displacement measuring device is sensitive to the moisture in the air. The maintenance of the apparatus accordingly is complicated, which leads to lower reliability.

SUMMARY OF THE INVENTION

It is an object of the present invention to resolve the problems of the prior art explained hereinbefore.

The object of the present invention is to provide an apparatus for determining the microhardness of a thin film of the order of 0.1 microns with high precision.

The other object of the present invention is to provide an apparatus for determination of microhardness, which can be effectively employed for quality control of production of semiconductor devices such as VLSI and magnetic recording discs.

According to the present invention, there is provided an apparatus for determining the microhardness of a specimen by measuring the penetration depth of an indenter into the specimen and the load applied to the indenter for penetrating the same into the specimen, which comprises:

- means for applying a load to the indenter to penetrate the indenter into the specimen;
- means for measuring the applied load to the indenter; and
- means for detecting the penetration depth of the indenter into the specimen and being connected integrally to the indenter to cooperate with the indenter.

According to a preferred embodiment of the present invention, the penetration-depth detecting means comprises:

- means for emitting a light beam to a predetermined position, the light emitting means being mounted so as to move together with the indenter, the level of said predetermined position being maintained unchanged with respect to the surface of the specimen;
- means for receiving the light beam reflected at said predetermined position;
- means for detecting the intensity of the received light beam to determine the penetration depth of the indenter from the variation of the intensity of the received light beam due to the movement of the indenter.

The penetration-depth detecting means may further comprise an optical fiber to which the light emitting means and the light receiving means are connected.

According to a preferred embodiment of the present invention, the apparatus further comprises a mirror at said predetermined position.

Preferably, the load-applying means includes a piezo-electric actuator. As for the load-measuring means, an electrobalance is most suitable used.

Specifically, the head of the indenter is in the shape of a trigonal pyramid which presents a vertical angle of about 80 degrees. The top portion of the head is preferably in the shape of a semi-sphere having a radius smaller than 0.1 microns, which can be formed by the ion-etching or ion-milling method.

Preferably, the apparatus further comprises a computer for controlling the load-applying means and for processing the data from the penetration-depth detecting means and the load detecting means.

For the purpose of controlling the load applying means, the apparatus comprises a D/A converter for converting the order signal from the computer into an analog signal, a constant-voltage source operative in response to the analog signal, a voltage amplifier for amplifying the signal from the constant-voltage source to actuate the load applying means.

In order to record the detected data, it is preferable that the apparatus further comprises an X-Y plotter for receiving respectively at the X and Y inputs thereof the data detected by the penetration-depth detecting means and the load-measuring means, and an X-Y recorder for recording respectively at the X axis and Y axis thereof the data detected by the penetration-depth detecting means and the load-measuring means.

The above and other objects, features and advantages of the present invention will be apparent from the following description of preferred embodiments of the invention with reference to the accompanying drawings.

DESCRIPTION OF PREFERRED EMBODIMENTS

Referring to the accompanying drawings, the present invention will be explained in detail in the following.

Figure 1:
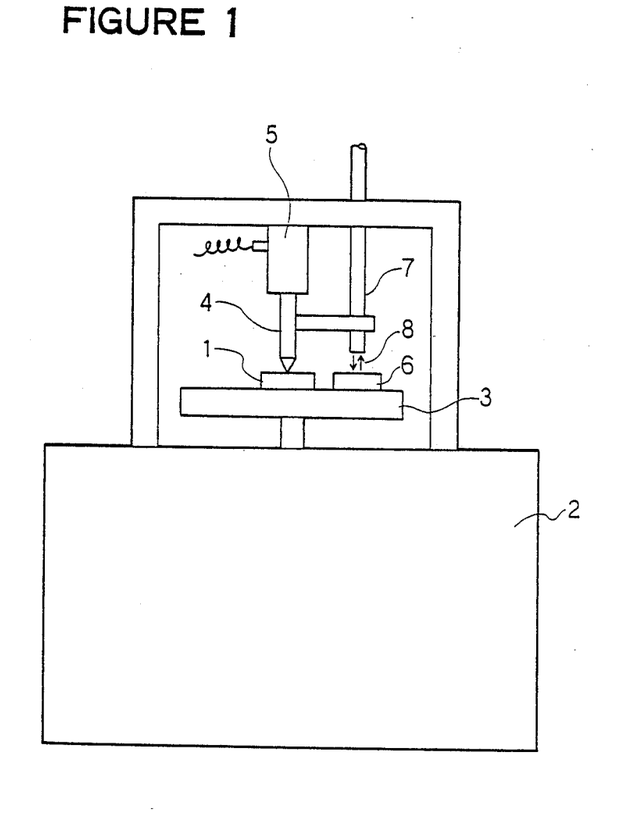
FIG. 1 is a schematic view of an example of the apparatus according to the present invention for determining the microhardness of a specimen.

FIG. 1 is a schematic view of an example of the apparatus according to the present invention for determining the microhardness of a specimen. The microhardness of a specimen 1 is determined by measuring the penetration depth of an indenter 4 into the specimen 1 and the load applied to the indenter 4 which is pressed into the specimen 1.

The head of the indenter 4 is in the shape of a trigonal pyramid so that the top portion of diamond can contact with the specimen 1 at a point. In reality, however, the top portion of the head of the indenter 4 presents usually a large radius of curvature. Therefore, the head portion is preferably processed by ion etching using argon ion to be in the shape of a semi-sphere having a radius between 0.01 and 0.1 microns. the vertical angle of the head is preferably as small as possible. In order to produce the indenter at a high production yield, however, it is preferable to process the head of the indenter to present a vertical angle around 80 degrees.

As shown in FIG. 1, the apparatus includes an electrobalance 2 for measuring the load with which the indenter 4 penetrates into the specimen 1. The electrobalance 2 is equipped with a sample dish 3 on which the specimen 1 is positioned, and is adapted to output in the form of digital signal the total weight or load applied to the sample dish 3. As well known in the art, the electrobalance 2 includes a detector for detecting the position of the sample dish shifted from the initial equilibrium state due to the weight or load applied thereto, and electromagnetic means for returning or restoring the sample dish to the initial equilibrium state by electromagnetic force. The load or weight is determined from the electric voltage which is applied to the electromagnetic means for returning the sample dish to the initial equilibrium state. The detector may be composed of a photodiode or photosensor.

The measuring resolution of the electrobalance is 0.1 micrograms. Therefore, the contact between the indenter 4 and the specimen 1 can be readily detected without applying load to the indenter. However, such a high measuring resolution is not necessary for measuring the microhardness of plastics or metals. For such a measurement, a resolution of about 0.01 milligrams is practically sufficient, and a conventional chemical balance or a strain gauge can be used as the means for measuring the applied load. However, the electrobalance is the most suitable, in view of precision and simplicity in handling.

The apparatus for determining the microhardness further includes a piezo-electric actuator 5 for applying load to the indenter 4, that is, for moving the indenter 4. The piezo-electric actuator 5 is connected at one end thereof to the indenter 4 and mounted on a frame member of the apparatus. The piezo-electric actuator 5 is composed of piezo-elements of a layered structure. The total length of the piezo-electric actuator 5 can be varied by changing the applied voltage. Thus, the penetration depth of the indenter 4 can be minutely controlled with a precision of 1 nanometer at a moving speed between 1 and 100 nanometers per second.

In the example illustrated in FIG. 1, the apparatus for determining the microhardness includes means for detecting the penetration depth of the indenter 4. As shown in FIG. 1, the penetration-depth detecting means comprises a mirror 6 fixed on the sample dish 3, a photonic probe (trade name) 7 emitting a light beam 8 to the mirror 6 and receiving the light beam 8 reflected at the mirror 6, and a photonic sensor (manufactured and saled by PHOTONICS Inc. USA in the trade name "photonic sensor") 16 (see FIG. 3) for detecting the reflected light beam 8. The photonic probe 7 is integrally connected to the indenter 4 so as to move together with the indenter 4.

The photonic probe 7 includes a optical fiber, a light emitting element and a photodetector connected to the optical fiber. Because the structure of the photonic probe 7 is well known in the art, however, it is not explained herein nor illustrated in the drawings. From the variation of the intensity of the reflected light beam 8, the displacement of the indenter with respect to the specimen 1, i.e. the penetration depth of the indenter 4 into the specimen 1 can be determined. The mirror 6 may be manufactured by forming a gold or a silver layer on a glass substrate by sputtering or vapor-deposition method.

By using the photonic sensor 16, high precision measurement can be performed without causing contact with the specimen 1 and without applying physical force to the specimen 1.

Various means may be employed for determining the penetration depth, but these means have drawbacks compared with the photonic sensor 16. For example, means for determining the penetration depth from the variation in static capacitance, the variation in reactance by electromagnetic induction or the variation in magnetic field can be used. However, with these penetration-depth detecting means, load must be applied to the specimen for the penetration-depth measurement. Therefore, high precision measurement is difficult to expect. In addition, these penetration-depth determining means are sensitive to the moisture in the air. An interferometer is also a candidate for determining the the penetration depth. In order to detect the variation of the order of 0.01 microns, the interferometer should be approached just near the specimen. Accordingly, it is difficult to perform measurement without causing contact between the interferometer and the specimen.

As described above, the indenter 4 to which the piezo-electric actuator 5 is fixed is integrally connected to the photonic probe 7 to move together. On the other hand, the electrobalance 2 is independently mounted of these means. Therefore, the electrobalance 2 is not at all influenced by the hysteresis of the piezo-electric actuator 5. Neither the piezo-electric actuator 5 nor the photonic probe 7 is influenced by the electrobalance 2.

Figure 2:
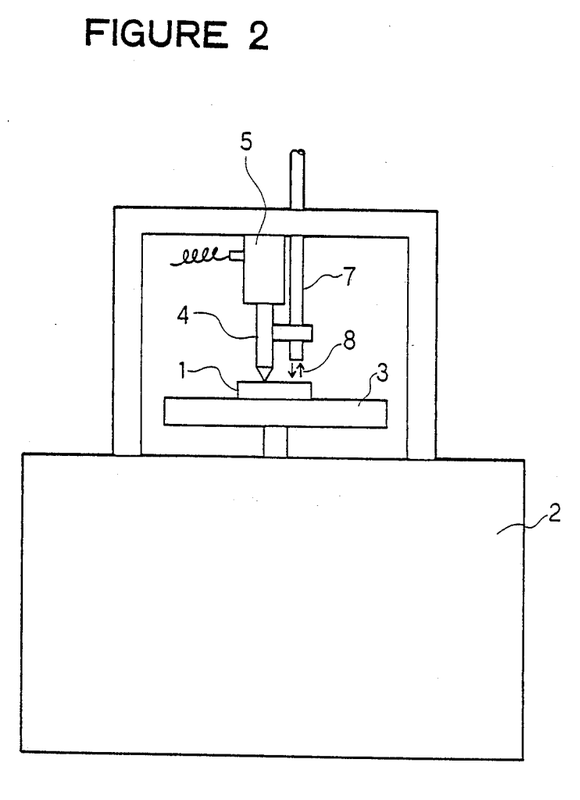
FIG. 2 is a schematic view of another example of the apparatus according to the present invention for determining the microhardness of a specimen.

FIG. 2 is a schematic view of another embodiment of the apparatus according to the present invention. The only difference between the apparatuses shown in FIG. 1 and FIG. 2 is that the photonic probe 7 is mounted just near the indenter 4 so that the light beam 8 emitted from the photonic probe 7 can be reflected by the surface of the specimen 1. Therefore, no mirror is fixed on the sample dish 3. In the case of the measurement of the microhardness of thin surface layers which present a high reflectivity, the light beam can be reflected at the surface of the specimen. Accordingly, the apparatus shown in FIG. 2 is preferably used for such a measurement.

The apparatus shown in FIGS. 1 and 2 further comprises a personal computer 9 for controlling the piezoelectric actuator 5 and for processing the data from the photonic probe 16 and the electrobalance 2.

Figure 3:
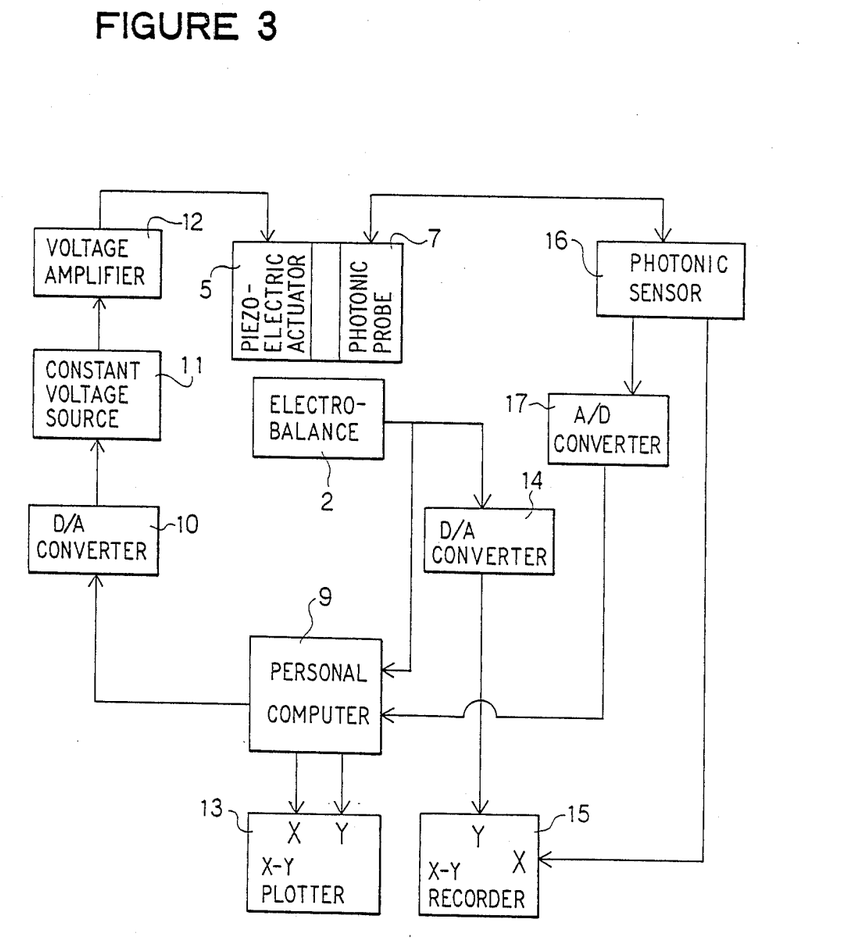
FIG. 3 is a block diagram of the apparatus for determining the microhardness of a specimen shown in FIG. 1.

FIG. 3 is a block diagram of the apparatus for illustrating the data processing in determining the microhardness.

For operating the piezo-electric actuator 5, the apparatus includes a D/A converter 10 for converting the order signal from the computer 9, a constant-voltage source 11 for outputting a signal of a constant voltage in response to the output signal from the D/A converter 10 and a voltage amplifier 12 for amplifying the output signal from the constant-voltage source to actuate the piezo-electric actuator 5.

For presenting and recording the data detected by the electrobalance 2 and the photonic sensor 16, the apparatus further includes an X-Y plotter 13 and an X-Y recorder 15. For representing and recording the detected data in analog form, a D/A converter 14 is provided between the electrobalance 2 and the X-Y recorder 15. On the other hand, and A/D converter 17 is provided between the photonic sensor 16 and the computer 9.

An order signal for actuating the piezo-electric actuator 5 is outputted from the personal computer 9 as a digital signal. The digital signal is converted to an analog signal by a D/A converter 10. The analog signal is then sent to a constant-voltage source 11. The output of the constant-voltage source 11 is amplified by a voltage amplifier 12 for controlling the piezo-electric actuator 5.

Weight signal from the electrobalance 2 is inputted to the Y input of an X-Y plotter 13 as a digital signal via the personal computer 9. Also, the same digital signal may be inputted to the Y input of an X-Y recorder 15 after converted to the analog signal by the D/A converter 14.

Light beam received by the photonic probe 7 is transmitted to the photonic sensor 16 through optical fibers for determining the penetration depth of the indenter 4 into the specimen 1. The photonic sensor 16 is for determining displacement based on the variation in the intensity of the reflected light beam. An analog signal from the photonic sensor 16 is inputted to the X input of the X-Y recorder 15. Also the same analog signal is inputted to the X input of the X-Y plotter 13 via the personal computer 9 after converted to a digital signal by the A/D converter 17.

Two examples for conducting measurement of the microhardness using the apparatus shown in FIGS. 1 and 3 are given in the following:

EXAMPLE 1

Sample No. 1 was prepared by sputtering a layer of thickness of 0.17 microns on a square glass substrate with 10×10 millimeters. Microhardness of the surface layer of this sample was determined by using the apparatus shown in FIGS. 1 and 3. The measuring resolution of the electrobalance is 10 micrograms, and that of the photonic probe 7 is 40 angstroms. The indenter 4 was pressed onto the sputtered layer by the piezo-electric actuator 5 at a speed of 7 nanometers per second.

Figure 4:
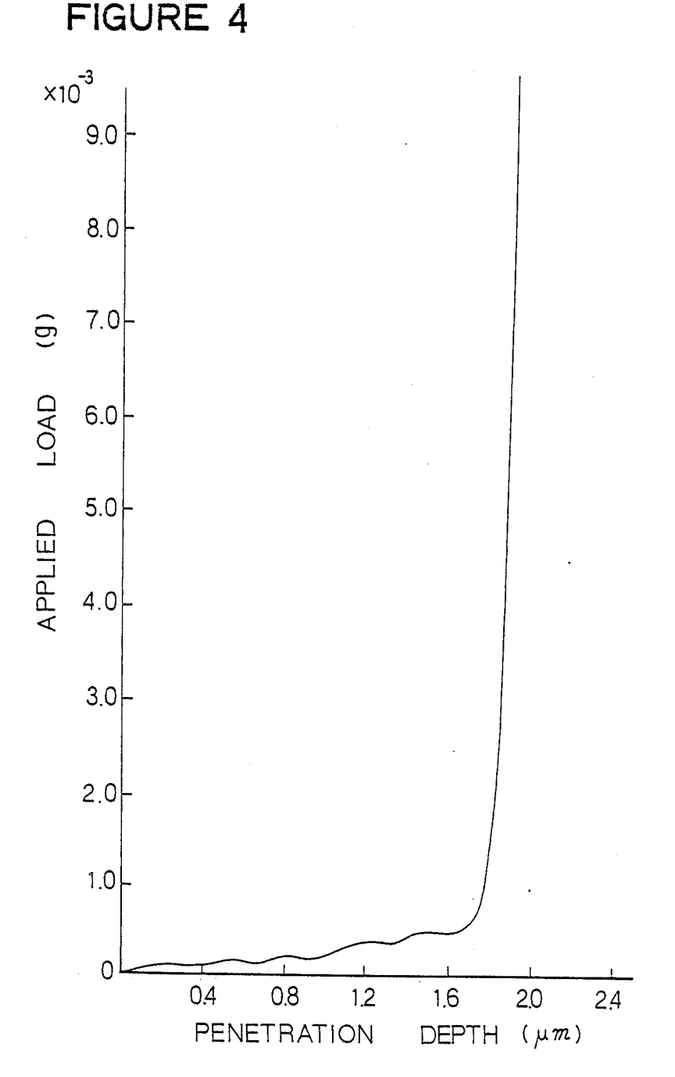
FIG. 4 is a graph showing the relation between the applied load and the penetration depth for a tin film on a glass substrate.

FIG. 4 is a graph showing the relation between the applied load and the penetration depth appeared on the X-Y recorder 15. As can be seen from FIG. 4, when the penetration depth is small, the applied load increases almost proportionally. However, at a certain penetration depth, applied load increases abruptly. The inflection point corresponds to the point where the indenter reaches the glass substrate. The microhardness of the tin film was thus determined to be $1.953 \times 10^6$ g/cm$^2$.

EXAMPLE 2

Sample No.2 was prepared by forming a cobalt layer of a thickness of 0.18 microns in the same manner as sample No. 1.

Figure 5:
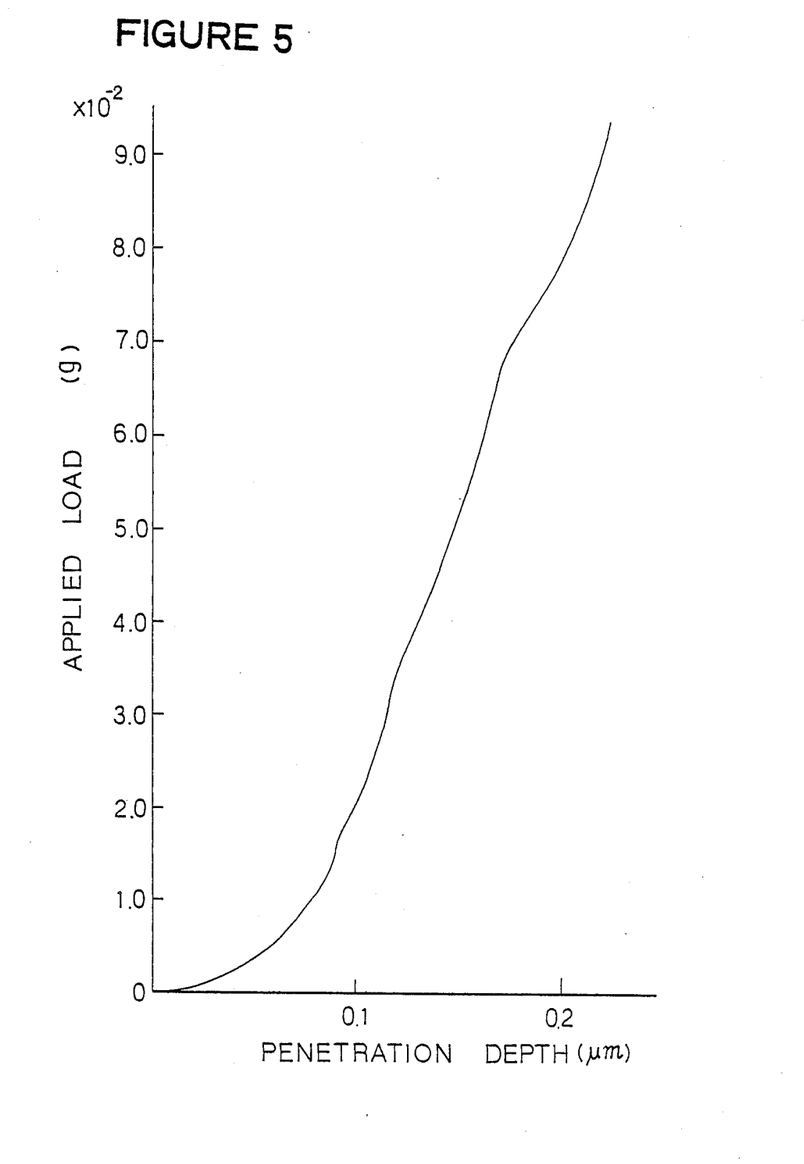
FIG. 5 is a graph showing the relation between the applied load and the penetration depth for a cobalt film on a glass substrate.

FIG. 5 is a graph showing the relation between the applied load and the penetration depth appeared on the X-Y recorder 15. The curve changes its curvature when the indenter reaches the glass substrate. The microhardness of the cobalt film was determined as $2.249 \times 10^8 \text{g/cm}^2$.

As known from the two examples, the depth where the microhardness changes can be precisely determined and the microhardness itself is determined with high precision.

The invention has thus been shown and described with reference to specific embodiments. However, it should be noted that the invention is in no way limited to the details of the illustrated structures but changes and modifications may be made within the scope of the appended claims.

We claim:

1. An apparatus for determining the microhardness of a specimen by measuring both a penetration depth of an indenter into the specimen and a load applied to the indenter for penetrating the same into the specimen, said apparatus comprising:

means connected directly in a straight line to the indenter for directly applying a load to the indenter in order to penetrate the indenter into the specimen;

means having a load receiving center located in alignment with the indenter and receiving the specimen which is penetrated by the indenter for measuring the load applied to the indenter; and means for detecting the penetration depth of the indenter into the specimen, the penetration-depth detecting means including means mounted to move together with the indenter for emitting a light beam to a predetermined position which is positioned at a level which is maintained unchanged with respect to the level of a surface of the specimen, means for receiving the light beam reflected from said predetermined position, and means for detecting the intensity of the received light beam to determine the penetration depth of the indenter in response to the variation of the intensity of the received light beam, said intensity variation being responsive to the displacement of the indenter.

2. An apparatus for determining the microhardness of a specimen by measuring both a penetration depth of an indenter into the specimen and a load applied to the indenter for causing it to penetrate into the specimen, said apparatus comprising:

means for applying an in line load directly toward a point on the indenter to penetrate the indenter in a straight line into the specimen;

means for measuring the load applied to the indenter; and means for detecting the penetration depth of the indenter into the specimen, the penetration-depth detecting means including an optical fiber integrally mounted on the indenter to move together with the indenter and having a light emitting and receiving end directed toward a predetermined position which is positioned at a level that is maintained unchanged with respect to the level of a surface of the specimen, means connected to the optical fiber for emitting a light beam through the optical fiber toward said predetermined position, means connected to the optical fiber for receiving through the optical fiber the light beam reflected at said predetermined position, and means for detecting the intensity of the received light beam to determine the penetration depth of the indenter in response to variations of the intensity of the received light beam due to the displacement of the indenter.

3. The apparatus as claimed in claim 2, wherein the penetration-depth detecting means further includes a mirror at said predetermined position.

4. The apparatus as claimed in claim 2, wherein the light beam is emitted to the surface of the specimen.

5. an apparatus for determining the microhardness of a specimen by measuring both a penetration depth of an indenter into the specimen and a load applied to the indenter for causing the load to penetrate into the specimen, said apparatus comprising:

a piezo-electric actuator directly connected in a straight line to the indenter for directly applying a load to the indenter in order to penetrate the indenter into the specimen;

means having a load receiving center located in alignment with the indenter and receiving the specimen which is penetrated by the indenter for measuring the load applied to the indenter; and means integrally connected to the indenter for detecting the displacement of the indenter to determine the penetration depth of the indenter into the specimen.

6. An apparatus for determining the microhardness of a specimen by measuring both the penetration depth of an indenter into the specimen and the load applied to the indenter for causing it to penetrate into the specimen, said apparatus comprising:

means for applying a load to the indenter to penetrate the indenter into the specimen;

means for measuring the load applied to the indenter; and means for integrally connected to the indenter for detecting the displacement of the indenter in order to determine the penetration depth of the indenter into the specimen, the indenter being in the shape of a trigonal pyramid having a head with a vertical angle of about 80 degrees, the top portion of the head of the indenter being in the shape of a semisphere having a radius which is smaller than 0.1 microns.

7. An apparatus for determining the microhardness of a specimen by measuring a penetration depth of an indenter into the specimen and a load applied to the indenter for causing it to penetrate into the specimen, said apparatus comprising:

means for applying a load to the indenter to penetrate the indenter into the specimen, the load applying means and said indenter being located along a straight line so that the load is applied axially to said indenter to drive it straight forward;

an electrobalance equipped with a sample dish on which the specimen is positioned, for measuring the load applied to the indenter; and means integrally connected to the indenter for detecting the displacement of the indenter in order to determine the penetration depth of the indenter into the specimen.

8. An apparatus for determining the microhardness of a specimen by measuring both a penetration depth of an indenter into the specimen and a load applied to the indenter for causing it to penetrate into the specimen, said apparatus comprising:

means axially aligned with said indenter for applying a load directly to the indenter to penetrate the indenter into the specimen;

means having a load receiving center located in alignment with the indenter and receiving the specimen which is penetrated by the indenter for measuring the load applied to the indenter;

means integrally connected to the indenter for detecting the displacement of the indenter to determine the penetration depth of the indenter into the specimen;

a computer for controlling the load-applying means and for processing data from the penetration-depth depth detecting means and the load-measuring means;

a digital-to-analog converter associated with a constant voltage source for converting an order signal from the computer into an analog voltage signal; and a voltage amplifier for receiving and amplifying the voltage signal, said voltage amplifier being coupled to the load-applying means to actuate the load-applying means.

9. The apparatus as claimed in claim 8, further comprising an X-Y plotter for receiving respectively at the X and Y inputs thereof the data detected by the penetration-depth detecting means and the load-measuring means.

10. The apparatus as claimed in claim 8, further comprising an X-Y recorder for recording respectively at the X axis and Y axis thereof the data detected by the penetration-depth detecting means and the load measuring means.

11. An apparatus for determining the microhardness of a specimen by measuring both the penetration depth of an indenter into the specimen and the load applied to the indenter for causing it to penetrate into the specimen, said apparatus comprising:

a piezo-electric actuator connected to the indenter for applying a load to the indenter to cause it to penetrate into the specimen;

an electrobalance equipped with a sample dish on which the specimen is positioned for measuring the load applied to the indenter; and means for optically detecting the displacement of the indenter to determine the penetration depth of the indenter into the specimen.

12. An apparatus as claimed in claim 11 wherein the penetration-depth detecting means includes an optical fiber integrally mounted on the indenter to move together with the indenter, said detecting means having a light emitting and receiving port directed toward a predetermined location which is positioned at a level that is maintained unchanged with respect to the level of a surface of the specimen, means connected to the optical fiber for emitting a light beam through the optical fiber toward said predetermined position, means connected to the optical fiber for receiving through the optical fiber the light beam reflected from said predetermined position, and means for detecting the intensity of the received light beam in order to determine the penetration depth of the indenter in response to variations of the intensity of the received light beam due to the displacement of the indenter.

* * * * *